United States Patent
Cowley et al.

(10) Patent No.: US 12,004,769 B2
(45) Date of Patent: Jun. 11, 2024

(54) ULTRASONIC TRANSDUCER ASSEMBLY FOR AN ULTRASONIC SURGICAL INSTRUMENT

(71) Applicant: Covidien LP, Mansfield, MA (US)

(72) Inventors: Matthew S. Cowley, Frederick, CO (US); David J. Van Tol, Boulder, CO (US)

(73) Assignee: Covidien LP, Mansfield, MA (US)

( * ) Notice: Subject to any disclaimer, the term of this patent is extended or adjusted under 35 U.S.C. 154(b) by 617 days.

(21) Appl. No.: 17/313,063

(22) Filed: May 6, 2021

(65) Prior Publication Data

US 2021/0361316 A1 Nov. 25, 2021

Related U.S. Application Data

(60) Provisional application No. 63/027,367, filed on May 20, 2020.

(51) Int. Cl.
*A61B 17/32* (2006.01)
*B06B 1/06* (2006.01)

(52) U.S. Cl.
CPC .......... *A61B 17/320092* (2013.01); *A61B 2017/320071* (2017.08); *B06B 1/0618* (2013.01)

(58) Field of Classification Search
CPC ........ A61B 17/320092; A61B 17/0618; A61B 17/320068; A61B 2017/320071; A61B 2017/320094
See application file for complete search history.

(56) References Cited

U.S. PATENT DOCUMENTS

| | | |
|---|---|---|
| 1,813,902 A | 7/1931 | Bovie |
| 2,235,274 A | 3/1941 | Trehern |
| 2,874,470 A | 2/1959 | Richards |
| 2,990,616 A | 7/1961 | Balamuth |
| 3,432,691 A | 3/1969 | Shoh |
| 3,489,930 A | 1/1970 | Shoh |
| 3,526,792 A | 9/1970 | Shoh |
| 3,629,726 A | 12/1971 | Popescu |
| 3,668,486 A | 6/1972 | Silver |
| 3,809,977 A | 5/1974 | Balamuth et al. |
| 3,875,945 A | 4/1975 | Friedman |
| 3,924,335 A | 12/1975 | Balamuth et al. |
| 4,012,647 A | 3/1977 | Balamuth et al. |
| 4,193,818 A | 3/1980 | Young et al. |

(Continued)

OTHER PUBLICATIONS

Extended European Search Report issued in corresponding European Application No. 21174920.5 dated Oct. 6, 2021, 6 pages.

*Primary Examiner* — Emily P Pham
(74) *Attorney, Agent, or Firm* — Carter, DeLuca & Farrell LLP (57) ABSTRACT

A ultrasonic transducer assembly of an ultrasonic surgical instrument includes a horn, a piezoelectric stack positioned proximally of the horn and defining a longitudinal opening extending therethrough, a proximal end mass positioned proximally of the piezoelectric stack and defining a longitudinal opening, and a rod secured to the horn and extending proximally from the horn through the longitudinal opening of the piezoelectric stack and the longitudinal opening of the proximal end mass. The rod is secured to the proximal end mass to pre-compress the piezoelectric stack between the horn and the proximal end mass.

14 Claims, 4 Drawing Sheets

(56) References Cited

U.S. PATENT DOCUMENTS

| | | |
|---|---|---|
| 4,227,110 A | 10/1980 | Douglas et al. |
| 4,300,083 A | 11/1981 | Heiges |
| 4,302,728 A | 11/1981 | Nakamura |
| 4,370,302 A | 1/1983 | Suzuoka et al. |
| 4,641,053 A | 2/1987 | Takeda |
| 5,113,116 A | 5/1992 | Wilson |
| 5,224,680 A | 7/1993 | Greenstein et al. |
| 5,264,925 A | 11/1993 | Shipp et al. |
| 5,275,166 A | 1/1994 | Vaitekunas et al. |
| 5,374,813 A | 12/1994 | Shipp |
| 5,394,187 A | 2/1995 | Shipp |
| 5,408,268 A | 4/1995 | Shipp |
| 5,451,220 A | 9/1995 | Ciervo |
| 5,490,860 A | 2/1996 | Middle et al. |
| 5,565,520 A | 10/1996 | Fock et al. |
| 5,582,617 A | 12/1996 | Klieman et al. |
| 5,593,414 A | 1/1997 | Shipp et al. |
| 5,685,311 A | 11/1997 | Hara |
| 5,717,306 A | 2/1998 | Shipp |
| 5,728,130 A | 3/1998 | Ishikawa et al. |
| 5,776,155 A | 7/1998 | Beaupre et al. |
| 5,792,138 A | 8/1998 | Shipp |
| 5,796,056 A | 8/1998 | Bredow et al. |
| 5,810,859 A | 9/1998 | DiMatteo et al. |
| 5,858,018 A | 1/1999 | Shipp et al. |
| 5,873,873 A | 2/1999 | Smith et al. |
| 5,897,569 A | 4/1999 | Kellogg et al. |
| 5,910,152 A | 6/1999 | Bays |
| 5,938,633 A | 8/1999 | Beaupre |
| 5,944,737 A | 8/1999 | Tsonton et al. |
| 5,947,984 A | 9/1999 | Whipple |
| 5,954,736 A | 9/1999 | Bishop et al. |
| 5,993,465 A | 11/1999 | Shipp et al. |
| 5,994,855 A | 11/1999 | Lundell et al. |
| 6,031,526 A | 2/2000 | Shipp |
| 6,036,667 A | 3/2000 | Manna et al. |
| 6,068,647 A | 5/2000 | Witt et al. |
| 6,095,981 A | 8/2000 | McGahan |
| 6,162,194 A | 12/2000 | Shipp |
| 6,183,426 B1 | 2/2001 | Akisada et al. |
| 6,220,098 B1 | 4/2001 | Johnson et al. |
| 6,254,623 B1 | 7/2001 | Haibel, Jr. et al. |
| 6,257,241 B1 | 7/2001 | Wampler |
| 6,278,218 B1 | 8/2001 | Madan et al. |
| 6,280,407 B1 | 8/2001 | Manna et al. |
| 6,283,981 B1 | 9/2001 | Beaupre |
| 6,284,185 B1 | 9/2001 | Tokuda et al. |
| 6,287,344 B1 | 9/2001 | Wampler et al. |
| 6,288,476 B1 | 9/2001 | Puskas |
| 6,290,575 B1 | 9/2001 | Shipp |
| 6,306,157 B1 | 10/2001 | Shchervinsky |
| 6,309,400 B2 | 10/2001 | Beaupre |
| 6,325,811 B1 | 12/2001 | Messerly |
| 6,328,751 B1 | 12/2001 | Beaupre |
| 6,350,269 B1 | 2/2002 | Shipp et al. |
| 6,352,532 B1 | 3/2002 | Kramer et al. |
| 6,416,486 B1 | 7/2002 | Wampler |
| 6,423,082 B1 | 7/2002 | Houser et al. |
| 6,432,118 B1 | 8/2002 | Messerly |
| 6,443,968 B1 | 9/2002 | Holthaus et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,482,220 B1 | 11/2002 | Mueller |
| 6,491,708 B2 | 12/2002 | Madan et al. |
| 6,500,188 B2 | 12/2002 | Harper et al. |
| 6,514,267 B2 | 2/2003 | Jewett |
| 6,537,291 B2 | 3/2003 | Friedman et al. |
| 6,561,983 B2 | 5/2003 | Cronin et al. |
| 6,565,520 B1 | 5/2003 | Young |
| 6,588,277 B2 | 7/2003 | Giordano et al. |
| 6,589,200 B1 | 7/2003 | Schwemberger et al. |
| 6,607,540 B1 | 8/2003 | Shipp |
| 6,623,500 B1 | 9/2003 | Cook et al. |
| 6,626,926 B2 | 9/2003 | Friedman et al. |
| 6,633,234 B2 | 10/2003 | Wiener et al. |
| 6,652,539 B2 | 11/2003 | Shipp et al. |
| 6,652,545 B2 | 11/2003 | Shipp et al. |
| 6,660,017 B2 | 12/2003 | Beaupre |
| 6,662,127 B2 | 12/2003 | Wiener et al. |
| 6,666,875 B1 | 12/2003 | Sakurai et al. |
| 6,678,621 B2 | 1/2004 | Wiener et al. |
| 6,679,899 B2 | 1/2004 | Wiener et al. |
| 6,719,776 B2 | 4/2004 | Baxter et al. |
| 6,752,815 B2 | 6/2004 | Beaupre |
| 6,773,444 B2 | 8/2004 | Messerly |
| 6,869,439 B2 | 3/2005 | White et al. |
| 6,908,472 B2 | 6/2005 | Wiener et al. |
| 6,915,623 B2 | 7/2005 | Dey et al. |
| 6,924,585 B2 | 8/2005 | Goodson |
| 6,945,981 B2 | 9/2005 | Donofrio et al. |
| 6,976,969 B2 | 12/2005 | Messerly |
| 7,037,306 B2 | 5/2006 | Podany et al. |
| 7,066,895 B2 | 6/2006 | Podany |
| 7,074,218 B2 | 7/2006 | Washington et al. |
| 7,108,695 B2 | 9/2006 | Witt et al. |
| 7,128,720 B2 | 10/2006 | Podany |
| 7,135,030 B2 | 11/2006 | Schwemberger et al. |
| 7,163,548 B2 | 1/2007 | Stulen et al. |
| 7,179,254 B2 | 2/2007 | Pendekanti et al. |
| 7,179,271 B2 | 2/2007 | Friedman et al. |
| 7,207,997 B2 | 4/2007 | Shipp et al. |
| 7,217,128 B2 | 5/2007 | Atkin et al. |
| 7,217,893 B1 | 5/2007 | Huang et al. |
| 7,230,199 B2 | 6/2007 | Chou et al. |
| 7,244,262 B2 | 7/2007 | Wiener et al. |
| 7,269,873 B2 | 9/2007 | Brewer et al. |
| 7,273,483 B2 | 9/2007 | Wiener et al. |
| 7,300,446 B2 | 11/2007 | Beaupre |
| 7,335,997 B2 | 2/2008 | Wiener |
| 7,337,010 B2 | 2/2008 | Howard et al. |
| 7,977,587 B2 | 7/2011 | Rajagopal et al. |
| 8,043,229 B2 | 10/2011 | Mulvihill et al. |
| 8,334,635 B2 | 12/2012 | Voegele et al. |
| 8,435,258 B2 | 5/2013 | Young et al. |
| 8,672,959 B2 | 3/2014 | Witt et al. |
| 10,966,744 B2 * | 4/2021 | Rhee .................. B06B 3/00 |
| 11,627,981 B2 * | 4/2023 | Cowley .......... A61B 17/320068 606/169 |
| 2001/0048855 A1 | 12/2001 | Lin |
| 2002/0002379 A1 | 1/2002 | Bishop |
| 2002/0055754 A1 | 5/2002 | Ranucci et al. |
| 2002/0077645 A1 | 6/2002 | Wiener et al. |
| 2002/0091339 A1 | 7/2002 | Horzewski et al. |
| 2003/0144680 A1 | 7/2003 | Kellogg et al. |
| 2003/0149424 A1 | 8/2003 | Barlev et al. |
| 2003/0199794 A1 | 10/2003 | Sakurai et al. |
| 2003/0212363 A1 | 11/2003 | Shipp |
| 2004/0097972 A1 | 5/2004 | Shipp et al. |
| 2004/0116952 A1 | 6/2004 | Sakurai et al. |
| 2004/0256487 A1 | 12/2004 | Collins et al. |
| 2005/0091770 A1 | 5/2005 | Mourad et al. |
| 2005/0107658 A1 | 5/2005 | Brockway |
| 2005/0113815 A1 | 5/2005 | Ritchie et al. |
| 2005/0119677 A1 | 6/2005 | Shipp |
| 2005/0149063 A1 | 7/2005 | Young et al. |
| 2005/0203329 A1 | 9/2005 | Muto et al. |
| 2005/0234338 A1 | 10/2005 | Masuda |
| 2005/0234484 A1 | 10/2005 | Houser et al. |
| 2006/0041220 A1 | 2/2006 | Boukhny et al. |
| 2006/0058825 A1 | 3/2006 | Ogura et al. |
| 2006/0079878 A1 | 4/2006 | Houser |
| 2006/0079879 A1 | 4/2006 | Faller et al. |
| 2006/0087286 A1 | 4/2006 | Phillips et al. |
| 2006/0129168 A1 | 6/2006 | Shipp |
| 2006/0178579 A1 | 8/2006 | Haynes |
| 2006/0178667 A1 | 8/2006 | Sartor et al. |
| 2006/0194567 A1 | 8/2006 | Kelly et al. |
| 2006/0206100 A1 | 9/2006 | Eskridge et al. |
| 2006/0217729 A1 | 9/2006 | Eskridge et al. |
| 2007/0011836 A1 | 1/2007 | Brewer et al. |
| 2007/0063618 A1 | 3/2007 | Bromfield |

(56) References Cited

U.S. PATENT DOCUMENTS

| | | |
|---|---|---|
| 2007/0149881 A1 | 6/2007 | Rabin |
| 2007/0166663 A1 | 7/2007 | Telles et al. |
| 2007/0175960 A1 | 8/2007 | Shelton et al. |
| 2007/0227866 A1 | 10/2007 | Dimig |
| 2007/0239028 A1 | 10/2007 | Houser et al. |
| 2007/0239101 A1 | 10/2007 | Kellogg |
| 2007/0282333 A1 | 12/2007 | Fortson et al. |
| 2008/0033248 A1 | 2/2008 | Akagi |
| 2008/0051693 A1 | 2/2008 | Babaev |
| 2008/0172076 A1 | 7/2008 | Chon et al. |
| 2008/0245841 A1 | 10/2008 | Smith et al. |
| 2009/0138006 A1 | 5/2009 | Bales et al. |
| 2009/0143797 A1 | 6/2009 | Smith et al. |
| 2009/0143805 A1 | 6/2009 | Palmer et al. |
| 2009/0223033 A1 | 9/2009 | Houser |
| 2010/0004669 A1 | 1/2010 | Smith et al. |
| 2010/0090420 A1 | 4/2010 | Nickels, Jr. et al. |
| 2010/0324581 A1 | 12/2010 | Mackool et al. |
| 2011/0040212 A1 | 2/2011 | Dietz et al. |
| 2011/0291526 A1 | 12/2011 | Abramovich et al. |
| 2012/0078278 A1 | 3/2012 | Bales, Jr. et al. |
| 2013/0338691 A1 | 12/2013 | Young et al. |
| 2014/0107684 A1 | 4/2014 | Craig |
| 2015/0148830 A1 | 5/2015 | Stulen et al. |
| 2015/0245850 A1 | 9/2015 | Hibner et al. |
| 2016/0331397 A1 | 11/2016 | Parham |
| 2016/0332004 A1 | 11/2016 | Shiotani et al. |
| 2017/0296216 A1 | 10/2017 | Du et al. |
| 2018/0055529 A1 | 3/2018 | Messerly et al. |
| 2019/0090900 A1 | 3/2019 | Rhee et al. |
| 2020/0107852 A1 | 4/2020 | Lee et al. |

\* cited by examiner

ULTRASONIC TRANSDUCER ASSEMBLY FOR AN ULTRASONIC SURGICAL INSTRUMENT

CROSS-REFERENCE TO RELATED APPLICATIONS

This application claims the benefit of, and priority to, U.S. Provisional Patent Application No. 63/027,367, filed on May 20, 2020, the entire contents of which are hereby incorporated herein by reference.

BACKGROUND

Technical Field

The present disclosure relates to ultrasonic surgical instruments and, more particularly, to an ultrasonic transducer assembly for an ultrasonic surgical instrument.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, and/or otherwise treat tissue.

Ultrasonic surgical instruments typically employ a transducer coupled to a handle of the ultrasonic surgical instrument and configured to produce ultrasonic energy for transmission along a waveguide to an end effector of the ultrasonic surgical instrument that is designed to treat tissue with the ultrasonic energy. The transducer may be driven by an ultrasonic generator that is on-board, e.g., on or within the handle of the ultrasonic surgical instrument, or remotely disposed, e.g., as a set-top box connected to the ultrasonic surgical instrument via an electrical cable. The end effector of the ultrasonic surgical instrument may include a blade that receives the ultrasonic energy from the waveguide for application to tissue and a jaw member configured to clamp tissue between the blade and the jaw member to facilitate treatment thereof.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is an ultrasonic transducer assembly of an ultrasonic surgical instrument including a horn, a piezoelectric stack positioned proximally of the horn and defining a longitudinal opening extending therethrough, a proximal end mass positioned proximally of the piezoelectric stack and defining a longitudinal opening extending therethrough, and a rod secured to the horn and extending proximally from the horn through the longitudinal opening of the piezoelectric stack and the longitudinal opening of the proximal end mass.

In an aspect of the present disclosure, the proximal end mass further defines a transverse lumen in communication with the longitudinal opening of the proximal end mass such that a portion of the rod is exposed through the transverse lumen. The exposed portion of the rod is fused to the proximal end mass within the transverse lumen to maintain a pre-compression of the piezoelectric stack between the horn and the proximal end mass.

In another aspect of the present disclosure, a proximal portion of the rod extends proximally from the proximal end mass and is fused to the proximal end mass.

In still another aspect of the present disclosure, the proximal end mass defines a plurality of transverse lumens in communication with the longitudinal opening of the proximal end mass such that a plurality of portions of the rod is exposed through the plurality of transverse lumens. In such aspects, the plurality of exposed portion of the rod is fused to the proximal end mass within the plurality of transverse lumens.

In yet another aspect of the present disclosure, an electrode assembly including at least one electrode is disposed between piezoelectric elements of the piezoelectric stack.

In still yet another aspect of the present disclosure, a distal end mass is disposed between the piezoelectric stack and the horn such that the piezoelectric stack is maintained in compression against the horn with the distal end mass disposed therebetween.

In another aspect of the present disclosure, the proximal end mass further defines a transverse lumen in communication with the longitudinal opening of the proximal end mass, the rod further defines a transverse lumen through a proximal portion thereof, and a wedge extends at least partially through the transverse lumen of the proximal end mass and the transverse lumen of the rod to maintain a pre-compression of the piezoelectric stack between the horn and the proximal end mass.

In yet another aspect of the present disclosure, a distal end portion of the rod is received within a proximally-facing cavity defined within the horn.

In another aspect of the present disclosure, the longitudinal opening of the proximal end mass is a tapered longitudinal opening, the rod further includes a distal body and an expandable proximal wedge at least partially received within the tapered longitudinal opening of the proximal end mass, and the expandable proximal wedge is configured to expand outwardly to thereby urge the proximal end mass distally to pre-compress the piezoelectric stack between the horn and the proximal end mass.

In still another aspect of the present disclosure, the expandable proximal wedge includes a threaded cavity and a threaded insert is configured for engagement within the threaded cavity to expand the proximal wedge outwardly. Alternatively, such an expandable wedge and threaded insert assembly may be utilized to, for example, secure the rod to the distal end mass or the ultrasonic horn to maintain a pre-compression of the piezoelectric stack. Likewise, any of the other pre-compression mechanisms detailed herein may be utilized to secure the rod to the distal end mass or the ultrasonic horn to maintain a pre-compression of the piezoelectric stack, rather than securing the rod and the proximal end mass.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1:
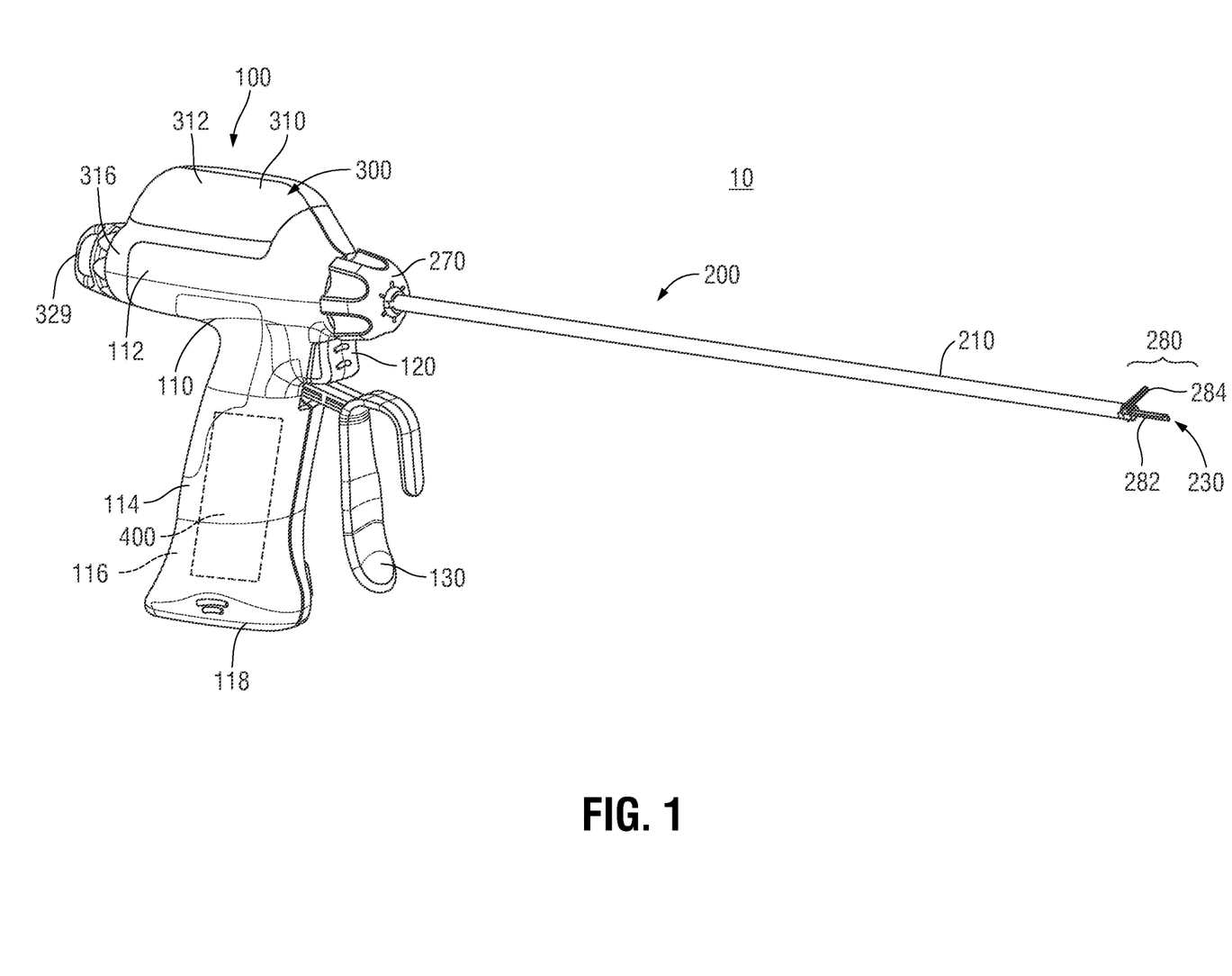
FIG. 1 is a side, perspective view of an ultrasonic surgical instrument provided in accordance with the present disclosure.
Figure 2:
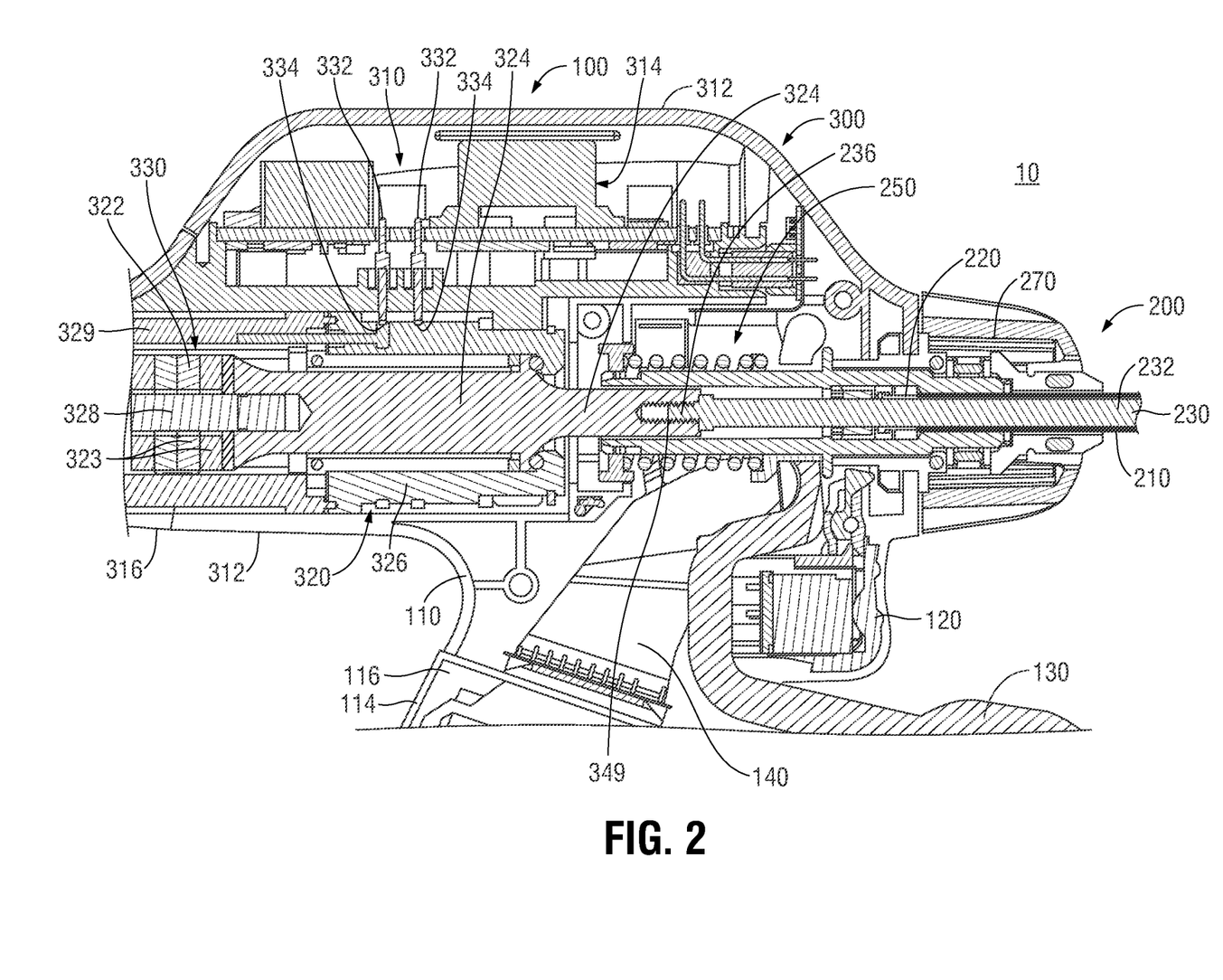
FIG. 2 is an enlarged, side, longitudinal, cross-sectional view of a proximal portion of the ultrasonic surgical instrument of FIG. 1.

Referring to FIGS. 1 and 2, an ultrasonic surgical instrument provided in accordance with aspects of the present disclosure is shown generally identified by reference numeral 10. Ultrasonic surgical instrument 10 includes a handle assembly 100 and an elongated assembly 200 extending distally from handle assembly 100. Handle assembly 100 includes a housing 110 defining a body portion 112 and a fixed handle portion 114. Handle assembly 100 further includes an activation button 120 and a clamp trigger 130.

Body portion 112 of housing 110 is configured to support an ultrasonic transducer and generator assembly ("TAG") 300 including a generator assembly 310 and an ultrasonic transducer assembly 320. TAG 300 may be permanently engaged with body portion 112 of housing 110 or removable therefrom. Generator assembly 310 includes a housing 312 configured to house the internal electronics 314 of generator assembly 310, and a cradle 316 configured to rotatably support ultrasonic transducer assembly 320. Alternatively, generator assembly 310 may be remotely disposed and coupled to ultrasonic surgical instrument 10 by way of a cable.

Ultrasonic transducer assembly 320 generally includes a piezoelectric stack 322, a horn 324, a casing 326, and an electrode assembly 330. Ultrasonic transducer 320 also includes a rotation knob 329. Casing 326 and rotation knob 329 are engaged with one another and cooperate to form an enclosure to encapsulate the internal components of ultrasonic transducer assembly 320 with a portion of horn 324 extending distally from casing 326. Rotation knob 329 is accessible from the exterior of handle assembly 100 and is configured for manual rotation to rotate ultrasonic transducer assembly 320 relative to generator assembly 310 and housing 110.

Continuing with reference to FIGS. 1 and 2, a set of connectors 332 and corresponding rotational contacts 334 associated with generator assembly 310 and ultrasonic transducer assembly 320, respectively, enable drive signals to be communicated from generator assembly 310 to piezoelectric stack 322 of ultrasonic transducer assembly 320 to drive ultrasonic transducer assembly 320 regardless of the rotational orientation of ultrasonic transducer assembly 320. More specifically, connectors 332 and rotational contacts 334 enable a drive signal voltage to be applied from generator assembly 310 across piezoelectric stack 322 via the positive and negative electrodes of electrode assembly 330. The piezoelectric stack 322, in turn, converts the applied voltage into mechanical energy, in the form of ultrasonic vibrations, that is transmitted to ultrasonic horn 324 (via the compression engagement therebetween, as detailed below).

Horn 324, in turn, is configured to transmit the ultrasonic energy produced by piezoelectric stack 322 to waveguide 230 of elongated assembly 200 for transmission therealong to blade 282 of end effector 280 of elongated assembly 200.

Referring still to FIGS. 1 and 2, fixed handle portion 114 of housing 110 defines a compartment 116 configured to receive a battery assembly 400 and a door 118 configured to enclose compartment 116. An electrical connection assembly 140 is disposed within housing 110 of handle assembly 100 and serves to electrically couple activation button 120, generator assembly 310 of TAG 300, and battery assembly 400 with one another when TAG 300 is supported on or in body portion 112 of housing 110 and battery assembly 400 is disposed within compartment 116 of fixed handle portion 114 of housing 110, thus enabling activation of ultrasonic surgical instrument 10 in response to depression of activation button 120. More specifically, when activation button 120 is activated in an appropriate manner, an underlying two-mode switch assembly of activation button 120 is activated to supply power from the battery assembly 400 to TAG 300 in either a "LOW" power mode or a "HIGH" power mode, depending upon the manner of activation of activation button 120. Activation button 120 may move in the same direction from an off position, to the "LOW" power mode, to the "HIGH" power mode or may move therebetween in any other suitable manner. Alternatively, separate activation buttons and/or different modes of operation are also contemplated.

Where generator assembly 310 is remote from ultrasonic surgical instrument 10, battery assembly 400 and the configuration of fixed handle portion 114 for receiving battery assembly 400 need not be provided, as generator assembly 310 may be powered by a standard wall outlet or other power source.

Elongated assembly 200 of ultrasonic surgical instrument 10 includes an outer drive sleeve 210, an inner support sleeve 220 disposed within outer drive sleeve 210, a waveguide 230 extending through inner support sleeve 220, a drive assembly 250, a rotation knob 270, and an end effector 280 including a blade 282 and a jaw 284. A proximal portion of outer drive sleeve 210 is operably coupled to clamp trigger 130 of handle assembly 100 via drive assembly 250, while a distal portion of outer drive sleeve 210 is operably coupled to jaw 284. As such, clamp trigger 130 is selectively actuatable to thereby move outer drive sleeve 210 about inner support sleeve 220 to pivot jaw 284 relative to blade 282 of end effector 280 from a spaced-apart position to an approximated position for clamping tissue between jaw 284 and blade 282. Drive assembly 250 provides a force-limiting feature whereby the clamping pressure applied to tissue is limited to a particular clamping pressure or particular clamping pressure range. Rotation knob 270 is rotatable in either direction to rotate elongated assembly 200 in either direction relative to handle assembly 100.

Waveguide 230, as noted above, extends through inner support sleeve 220. Waveguide 230 defines a body 232 and a blade 282 extending from the distal end of body 232. Blade 282 serves as the blade of end effector 280. Waveguide 230 further includes a proximal threaded male connector 236 configured for threaded engagement within threaded female receiver 349 of horn 324 such that ultrasonic motion produced by ultrasonic transducer assembly 320 is transmitted along waveguide 230 to blade 282 for treating tissue clamped between blade 282 and jaw 284 or positioned near blade 282. Other suitable engagements between waveguide 230 and horn 324 are also contemplated.

Figure 3:
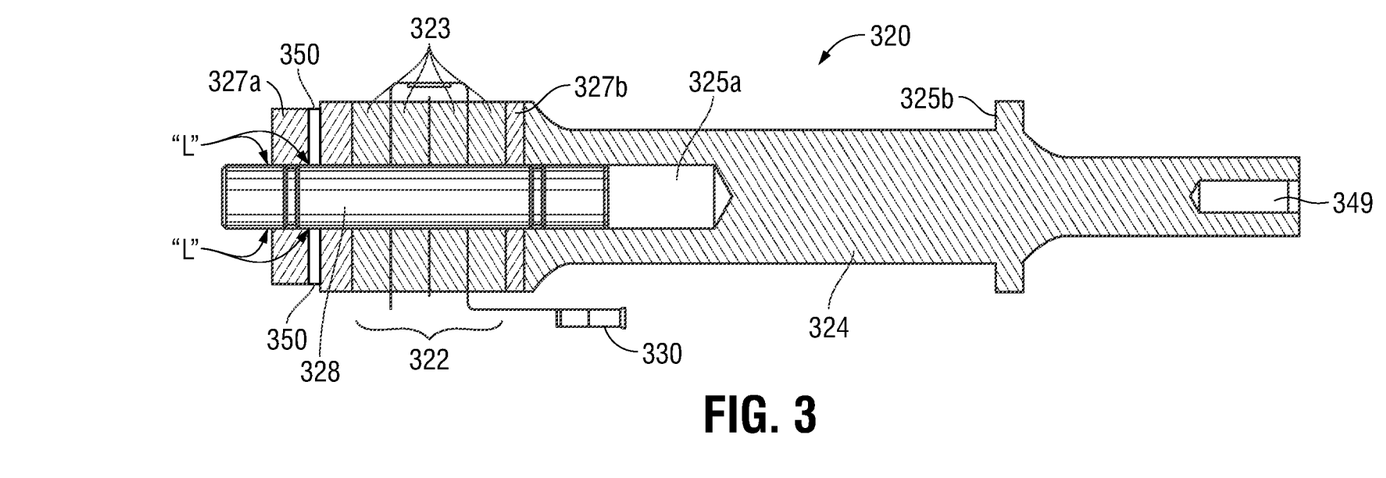
FIG. 3 is a longitudinal, cross-sectional view of the ultrasonic transducer assembly of ultrasonic surgical instrument of FIG. 1.

Turning to FIG. 3, ultrasonic transducer assembly 320, more specifically, includes piezoelectric stack 322, horn 324, casing 326 (FIG. 2), proximal and distal end masses 327a, 327b, and a rod 328 securing piezoelectric stack 322 between proximal and distal end masses 327a, 327b, respectively, and to horn 324 under compression. The pre-compression of piezoelectric stack 322 against horn 324 (directly or indirectly), enables efficient and effective transmission of ultrasonic energy from piezoelectric stack 322 to horn 324 for transmission along waveguide 230 to blade 282 for treating tissue clamped between blade 282 and jaw 284 or positioned near blade 282 (see FIGS. 1 and 2). Ultrasonic transducer assembly 320 further includes electrode assembly 330 having at least one electrode disposed in contact with a surface of at least one piezoelectric element 323 of piezoelectric stack 322 and at least one electrode disposed in contact with an opposed surface of the at least one piezoelectric element 323 of piezoelectric stack 322 to, as noted above, enable a drive signal voltage to be applied across piezoelectric stack 322. In some configurations, distal end mass 327a is omitted and horn 324 acts as the distal end mass against which piezoelectric stack 322 is directly compressed.

Rod 328, as noted above, secures piezoelectric stack 322 between proximal and distal end masses 327a, 327b, respectively, and to horn 324 under compression. This is accomplished via securement of rod 328 at a distal end portion thereof to horn 324 and at a proximal end portion thereof to proximal end mass 327a. Alternatively, rod 328 and horn 324 may be integrally formed as a single, monolithic component prior to assembly of ultrasonic transducer assembly 320. As such, securement of rod 328 at a distal end portion thereof to horn 324 during assembly is not required as rod 328 is already formed with horn 324. Proximal and/or distal end masses 327a, 327b, respectively, may define disc-shaped configurations or any other configurations, and include central openings to enable longitudinal receipt of rod 328 therethrough.

To assemble ultrasonic transducer assembly 320, the electrodes of electrode assembly 330 are interdisposed between piezoelectric elements 323 of piezoelectric stack 322 and proximal and distal end masses 327a, 327b are arranged at the proximal end distal ends, respectively, of piezoelectric stack 322. A distal end portion of rod 328 is secured within a proximally-facing cavity 325a defined within horn 324, e.g., via threaded engagement, welding, press-fitting, combinations thereof, or in any other suitable manner. Alternatively, as noted above, rod 328 and horn 324 may be integrally formed, obviating the need for this securement. Further still, rod 328 may be integrally formed with distal end mass 327b. The electrodes of electrode assembly 330, piezoelectric elements 323, and proximal and distal end masses 327a, 327b are disposed about rod 328, e.g., with rod 328 received longitudinally through the central openings thereof, and positioned such that distal end mass 327b abuts horn 324. Some or all of the above steps may be performed in the order detailed above, in any other suitable order, simultaneously, and/or in overlapping temporal relation relative to one another.

Regardless of the particular order of steps, the above results in a configuration wherein the distal end portion of rod 328 is secured within proximally-facing cavity 325a of horn 324 and wherein distal end mass 327b, piezoelectric stack 322 (including the electrodes of electrode assembly 330 interdisposed between piezoelectric elements 323 of piezoelectric stack 322), and proximal end mass 327a are disposed about rod 328 in a distal-to-proximal direction extending from horn 324. Once this position has been achieved, the assembly may be loaded into a fixture (not shown) whereby the fixture contacts and retains the assembly at a distal location such as at horn 324 and at a proximal location such as at proximal end mass 327a.

With the fixture retaining the assembly, the fixture may then be manipulated, actuated, or otherwise adjusted to apply a longitudinal compressive force to the assembly until a suitable pre-compression of piezoelectric stack 322 between proximal end mass 327a and horn 324 is achieved. Since the piezoelectric stack 322 produces a voltage as it is compressed, the longitudinal compressive force may be applied until a pre-determined voltage by the piezoelectric stack 322 is measured or until a voltage within a pre-determined voltage range is measured. This voltage or voltage range may correspond to a pre-determined pre-compression force or pre-compression force range. Alternatively, a force gauge may be utilized to determine the pre-compression force.

Continuing with reference to FIG. 3, once the desired pre-compression force (or a pre-compression force within a desired range) is reached, the fixture is locked or otherwise maintained to retain the assembly in position, thereby maintaining the piezoelectric stack 322 between proximal end mass 327a and horn 324 under compression. Thereafter, the proximal end portion of rod 328 is secured to proximal end mass 327a, for example, by fusing, e.g., welding, in one or more locations "L" at the interface between rod 328 and proximal end mass 327a, e.g., in one or more annular positions about the circumference of rod 328 adjacent the proximal face of proximal end mass 327a.

Proximal end mass 327a includes one or more transverse lumens 350 defined transversely therethrough in communication with the central opening thereof such that transverse lumens 350 expose portions of rod 328 extending through the central opening of proximal end mass 327a. These exposed portions of rod 328 provide additional fusing, e.g., welding, locations "L" to enable the proximal end portion of rod 328 to be secured to proximal end mass 327a, e.g., in one or more annular positions about the circumference of rod 328 adjacent the proximal and/or distal internal faces of proximal end mass 327a that define each transverse lumen 350. The fuse locations "L" established by transverse lumens 350 are not limited to any specific locations within transverse lumens 350; rather, any suitable location or locations "L" defined by transverse lumens 350 may be utilized. Any suitable number of transverse lumens 350 may be provided in any suitable arrangement, e.g., a pair of diametrically opposed apertures, four apertures disposed at 0, 90, 180, and 270 degrees about proximal end mass 327a, and/or other radially symmetric or non-symmetric arrangements. Further, transverse lumens 350 need not be disposed perpendicular to a longitudinal axis of rod 328 by may be disposed at any suitable angle that intersects the central opening of proximal end mass 327a and, thus, expose portions of rod 328.

In some configurations, rather than the fuse locations "L" established by transverse lumens 350 serving as additional fuse locations "L," rod 328 and proximal end mass 327a may be fused to one another only using the fuse locations "L" defined by transverse lumens 350. Likewise, rather than fusing at the proximal interface between rod 328 and proximal end mass 327a (where rod 328 emerges from the proximal end of the central opening defined through proximal end mass 327a), rod 328 and proximal end mass 327a may be secured at this proximal interface in another suitable manner, e.g., via a threaded nut engaged about a threaded portion of rod 328. In any of the above configurations, securing rod 328 and proximal end mass 327a at the fuse locations "L" defined by transverse lumens 350 (itself or in addition to other securements) helps maintain the pre-determined pre-compression force or compression force of piezoelectric stack 322 between proximal end mass 327a and horn 324. It is noted that the pre-determined pre-compression force or compression force within a pre-determined compression force range applied during assembly does not necessarily equal the maintained compression force, e.g., due to expansion or stretching of component(s) upon release, temperature, etc.; thus, the pre-determined pre-compression force or pre-compression force within a pre-determined pre-compression range may be selected to achieve a resultant maintained compression force.

Once the above assembly is complete, casing 326 and rotation knob 329 may be positioned about the assembly and secured thereabout to complete the assembly of ultrasonic transducer assembly 320 (see FIG. 2).

Figure 4:
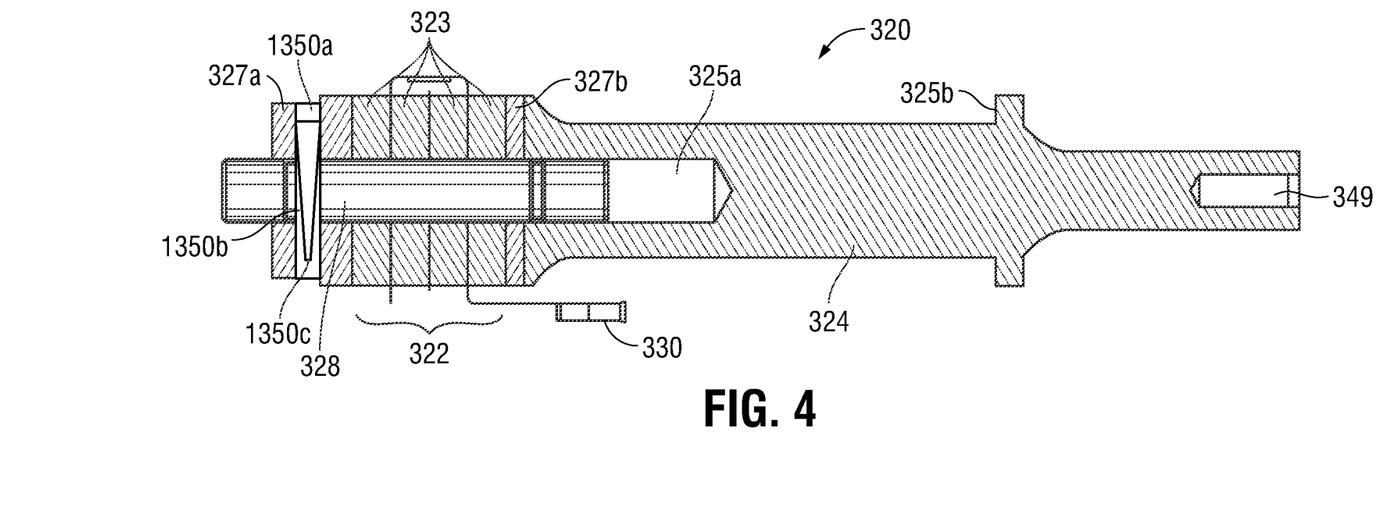
FIG. 4 is a longitudinal, cross-sectional view of another ultrasonic transducer assembly configured for use with the ultrasonic surgical instrument of FIG. 1.

Referring to FIG. 4, another mechanism for use with ultrasonic transducer assembly 320 to maintain the piezoelectric stack 322 between proximal end mass 327a and horn 324 under compression is shown generally including a transverse lumen 1350a defined at least partially through proximal end mass 327a and communicating with the central aperture thereof. In some configurations, transverse lumen 1350a extends completely through proximal end mass 327a. Rod 328 likewise includes a transverse lumen 1350b defined therethrough towards the proximal end thereof.

With respect to assembly, as with the assembly of ultrasonic transducer assembly 320 detailed above with respect to FIG. 3, the distal end portion of rod 328 is secured within proximally-facing cavity 325a of horn 324, e.g., via threaded engagement, welding, press-fitting, combinations thereof, integral formation, or in any other suitable manner, and distal end mass 327b, piezoelectric stack 322 (including the electrodes of electrode assembly 330 interdisposed between piezoelectric elements 323 of piezoelectric stack 322), and proximal end mass 327a are disposed about rod 328 in a distal-to-proximal direction extending from horn 324.

Once the above assembly has been achieved, transverse lumen 1350b of rod 328 and transverse lumen 1350a of proximal end mass 327a are partially overlapping with one another, with or without the need to applying compressive force as detailed above with respect to FIG. 3.

Continuing with reference to FIG. 4, once transverse lumen 1350b of rod 328 and transverse lumen 1350a of proximal end mass 327a are partially overlapping, a wedge 1350c is driven through transverse lumen 1350a of proximal end mass 327a and into transverse lumen 1350b of rod 328. The driving of wedge 1350c through transverse lumen 1350a and into transverse lumen 1350b urges rod 328 proximally and/or proximal end mass 327a distally relative to one another to thereby apply a pre-compression between proximal end mass 327a and horn 324. Wedge 1350c may be a tapered pin or other suitable structure that serves to increase the pre-compression between proximal end mass 327a and horn 324 upon further driving through transverse lumen 1350a and into transverse lumen 1350b.

Wedge 1350 may be driven to a pre-determined position or may be driven until a desired pre-compression or pre-compression within a desired pre-compression range of piezoelectric stack 322 between proximal end mass 327a and horn 324 is achieved. The pre-compression may be measured via voltage sensing, as detailed above, or in any other suitable manner. In some configurations, fusing, e.g., welding, rod 328 and proximal end mass 327a and/or wedge 1350c and proximal end mass 327a, or otherwise further securing rod 328, proximal end mass 327a, and/or wedge 1350c relative to one another may be provided to further retain the relative positions therebetween and maintain the pre-compression between proximal end mass 327a and horn 324.

Once the above assembly is complete, casing 326 and rotation knob 329 may be positioned about the assembly and secured thereabout to complete the assembly of ultrasonic transducer assembly 320 (see FIG. 2).

Figure 5:
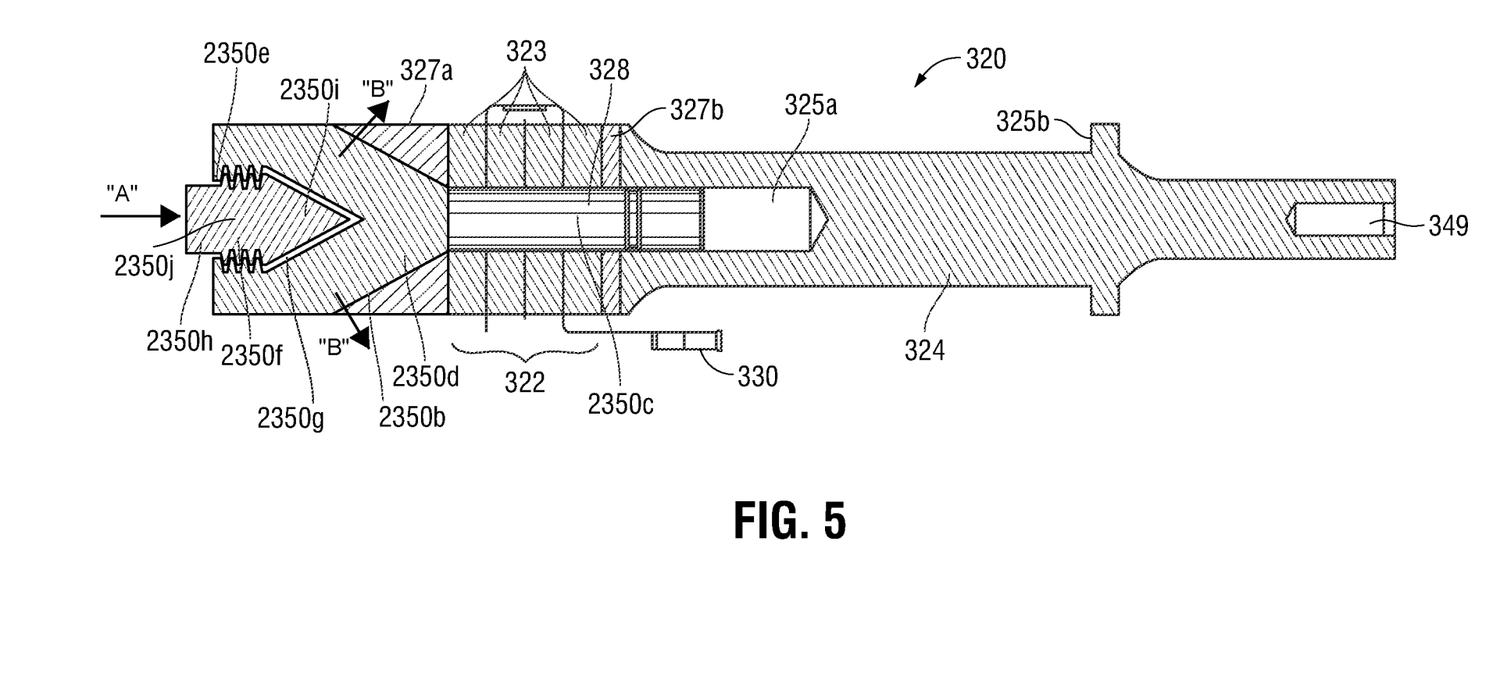
FIG. 5 is a longitudinal, cross-sectional view of another ultrasonic transducer assembly configured for use with the ultrasonic surgical instrument of FIG. 1.

With reference to FIG. 5, another mechanism for use with ultrasonic transducer assembly 320 to maintain the piezoelectric stack 322 between proximal end mass 327a and horn 324 under compression is shown wherein proximal end mass 327a defines a tapered central opening 2350b that tapers in inner diameter in a proximal-to-distal direction. Rod 328 includes a cylindrical distal body portion 2350c and a proximal wedge portion 2350d that tapers in outer diameter in a proximal-to-distal direction. Cylindrical distal body portion 2350c and proximal wedge portion 2350d may be monolithically formed together as a single piece, or may be separately formed and subsequently joined, e.g., via welding. Proximal wedge portion 2350d of rod 328 further includes a proximal cavity 2350e defined therein including a threaded cylindrical portion 2350f open to the open proximal end of proximal cavity 2350e, and a tapered portion 2350g tapering in a proximal-to-distal direction and extending distally from the threaded cylindrical portion 2350f to a closed distal end of proximal cavity 2350e. An insert 2350h defining a tapered distal portion 2350i tapering in a proximal-to-distal direction and a threaded cylindrical portion 2350j extending proximally from tapered distal portion 2350i is configured for threaded engagement within proximal cavity 2350e.

With respect to assembly, as with the assembly of ultrasonic transducer assembly 320 detailed above with respect to FIG. 3, the cylindrical distal body portion 2350c of rod 328 is secured within proximally-facing cavity 325a of horn 324, e.g., via threaded engagement, welding, press-fitting, combinations thereof, integral formation, or in any other suitable manner, and distal end mass 327b, piezoelectric stack 322 (including the electrodes of electrode assembly 330 interdisposed between piezoelectric elements 323 of piezoelectric stack 322), and proximal end mass 327a are disposed about rod 328 in a distal-to-proximal direction extending from horn 324.

Since the maximum outer diameter of proximal wedge portion 2350d of rod 328 is sufficiently great so as to inhibit passage through the minimum inner diameter of tapered central opening 2350b of proximal end mass 327a, the above-detailed portion of assembly may be achieved by first inserting rod 328 distally through proximal end mass 327a, piezoelectric stack 322 (including the electrodes of electrode assembly 330), and distal end mass 327b, and thereafter securing the cylindrical distal body portion 2350c of rod 328 within proximally-facing cavity 325a of horn 324. Other suitable orders and/or manners of securement are also contemplated.

Once the above-detailed portion of assembly has been achieved, insert 2350h is threaded into engagement at least partially within or further threaded into engagement at least partially within proximal cavity 2350e of proximal wedge portion 2350d of rod 328 to advance insert 2350h distally within proximal cavity 2350e and relative to proximal wedge portion 2350d of rod 328, e.g., as indicated by arrow "A." As a result of the tapered configurations of insert 2350*h* and proximal cavity 2350*e*, distal advancement of insert 2350*h* urges proximal wedge portion 2350*d* of rod 328 to expand outwardly, e.g., as indicated by arrows "B." This outward expansion of proximal wedge portion 2350*d* of rod 328, in turn, and due to the tapered configurations of proximal wedge portion 2350*d* of rod 328 and tapered central opening 2350*b* of proximal end mass 327*a*, urges proximal end mass 327*a* distally, thereby compressing piezoelectric stack 322 between proximal end mass 327*a* and horn 234. It is noted that a fixture (not shown) or other suitable structure(s) may be utilized to maintain horn 234 in substantially fixed position as proximal end mass 327*a* is urged distally, such that compression of piezoelectric stack 322 is achieved.

Insert 2350*h* may be driven to a pre-determined position or may be driven until a desired pre-compression or pre-compression within a desired pre-compression range of piezoelectric stack 322 between proximal end mass 327*a* and horn 324 is achieved. The pre-compression may be measured via voltage sensing, as detailed above, or in any other suitable manner. In some configurations, fusing, e.g., welding, or otherwise securing rod 328, proximal end mass 327*a*, and/or insert 2350*h* relative to one another may be provided to further retain the relative positions therebetween and maintain the pre-compression between proximal end mass 327*a* and horn 324. Further, as an alternative to threaded engagement of insert 2350*h* within proximal cavity 2350*e*, insert 2350*h* may be slid, e.g., wedged, into proximal cavity 2350*e*, increasing expanding proximal wedge portion 2350*d*, and then fused, e.g., welded, in position once the desired pre-compression of piezoelectric stack 322 is achieved. In such configurations, a compression fixture (not shown) may be utilized to retain the assembly and drive the sliding of insert 2350*h* into proximal cavity 2350*e*.

Once the above assembly is complete, casing 326 and rotation knob 329 may be positioned about the assembly and secured thereabout to complete the assembly of ultrasonic transducer assembly 320 (see FIG. 2).

Referring back to FIG. 1, as opposed to a handle assembly 100 for handheld, manual manipulation and operation, the aspects and features of the present disclosure are also applicable for use with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.). The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

While several aspects and features of the disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications. Those skilled in the art will envision other modifications within the scope and spirit of the claims appended hereto.

What is claimed is:

1. An ultrasonic transducer assembly of an ultrasonic surgical instrument, comprising:
   a horn;
   a piezoelectric stack positioned proximally of the horn and defining a longitudinal opening extending therethrough;
   a proximal end mass positioned proximally of the piezoelectric stack and defining a longitudinal opening extending therethrough, the proximal end mass further defining a transverse lumen in communication with the longitudinal opening of the proximal end mass; and
   a rod secured to the horn and extending proximally from the horn through the longitudinal opening of the piezoelectric stack and the longitudinal opening of the proximal end mass such that a portion of the rod is exposed through the transverse lumen,
   wherein the exposed portion of the rod is fused to the proximal end mass within the transverse lumen to maintain a pre-compression of the piezoelectric stack between the horn and the proximal end mass.

2. The ultrasonic transducer assembly according to claim 1, wherein a proximal portion of the rod extends proximally from the proximal end mass, and wherein the proximal portion of the rod is fused to the proximal end mass.

3. The ultrasonic transducer assembly according to claim 1, wherein the proximal end mass defines a plurality of transverse lumens in communication with the longitudinal opening of the proximal end mass such that a plurality of portions of the rod is exposed through the plurality of transverse lumens, and wherein the plurality of exposed portion of the rod is fused to the proximal end mass within the plurality of transverse lumens.

4. The ultrasonic transducer assembly according to claim 1, further comprising an electrode assembly including at least one electrode disposed between piezoelectric elements of the piezoelectric stack.

5. The ultrasonic transducer assembly according to claim 1, further comprising a distal end mass disposed between the piezoelectric stack and the horn, wherein the piezoelectric stack is maintained in compression against the horn with the distal end mass disposed therebetween.

6. An ultrasonic transducer assembly of an ultrasonic surgical instrument, comprising:
   a horn;
   a piezoelectric stack positioned proximally of the horn and defining a longitudinal opening extending therethrough;
   a proximal end mass positioned proximally of the piezoelectric stack and defining a longitudinal opening extending therethrough, the proximal end mass further defining a transverse lumen in communication with the longitudinal opening of the proximal end mass;
   a rod secured to the horn and extending proximally from the horn through the longitudinal opening of the piezoelectric stack and the longitudinal opening of the proximal end mass, the rod defining a transverse lumen through a proximal portion thereof; and
   a wedge extending at least partially through the transverse lumen of the proximal end mass and the transverse lumen of the rod to maintain a pre-compression of the piezoelectric stack between the horn and the proximal end mass.

7. The ultrasonic transducer assembly according to claim 6, wherein a distal end portion of the rod is received within a proximally-facing cavity defined within the horn.

8. The ultrasonic transducer assembly according to claim 6, further comprising an electrode assembly including at least one electrode disposed between piezoelectric elements of the piezoelectric stack.

9. The ultrasonic transducer assembly according to claim 6, further comprising a distal end mass disposed between the piezoelectric stack and the horn, wherein the piezoelectric stack is maintained in compression against the horn with the distal end mass disposed therebetween.

10. An ultrasonic transducer assembly of an ultrasonic surgical instrument, comprising:
    a horn;
    a piezoelectric stack positioned proximally of the horn and defining a longitudinal opening extending therethrough;
    a proximal end mass positioned proximally of the piezoelectric stack and defining a tapered longitudinal opening extending therethrough;
    a rod secured to the horn and extending proximally from the horn through the longitudinal opening of the piezoelectric stack and the tapered longitudinal opening of the proximal end mass, the rod including a distal body and an expandable proximal wedge, the expandable proximal wedge at least partially received within the tapered longitudinal opening of the proximal end mass,
    wherein the expandable proximal wedge is configured to expand outwardly to thereby urge the proximal end mass distally to pre-compress the piezoelectric stack between the horn and the proximal end mass.

11. The ultrasonic transducer assembly according to claim 10, wherein the expandable proximal wedge includes a threaded cavity, and wherein a threaded insert is configured for engagement within the threaded cavity to expand the proximal wedge outwardly.

12. The ultrasonic transducer assembly according to claim 10, wherein a distal end portion of the rod is received within a proximally-facing cavity defined within the horn.

13. The ultrasonic transducer assembly according to claim 10, further comprising an electrode assembly including at least one electrode disposed between piezoelectric elements of the piezoelectric stack.

14. The ultrasonic transducer assembly according to claim 10, further comprising a distal end mass disposed between the piezoelectric stack and the horn, wherein the piezoelectric stack is maintained in compression against the horn with the distal end mass disposed therebetween.

\* \* \* \* \*